United States Patent
Shimo

(10) Patent No.: US 9,452,971 B2
(45) Date of Patent: Sep. 27, 2016

(54) MANUFACTURING PROCESS FOR MEMANTINE

(71) Applicant: Mitsubishi Gas Chemical Company, Inc., Chiyoda-ku (JP)

(72) Inventor: Tetsuya Shimo, Niigata (JP)

(73) Assignee: MITSUBISHI GAS CHEMICAL COMPANY, INC., Chiyoda-ku (JP)

( * ) Notice: Subject to any disclaimer, the term of this patent is extended or adjusted under 35 U.S.C. 154(b) by 0 days.

(21) Appl. No.: 14/762,566

(22) PCT Filed: Jan. 16, 2014

(86) PCT No.: PCT/JP2014/050716
§ 371 (c)(1),
(2) Date: Jul. 22, 2015

(87) PCT Pub. No.: WO2014/115638
PCT Pub. Date: Jul. 31, 2014

(65) Prior Publication Data
US 2015/0368183 A1 Dec. 24, 2015

(30) Foreign Application Priority Data
Jan. 23, 2013 (JP) ................................. 2013-010125

(51) Int. Cl.
*C07C 209/62* (2006.01)
*C07C 231/06* (2006.01)

(52) U.S. Cl.
CPC ........... *C07C 209/62* (2013.01); *C07C 231/06* (2013.01)

(58) Field of Classification Search
None
See application file for complete search history.

(56) References Cited

U.S. PATENT DOCUMENTS

| 2006/0173215 A1 | 8/2006 | Merli et al. |
| 2009/0082596 A1 | 3/2009 | Schickaneder |
| 2012/0259128 A1 | 10/2012 | Ogawa et al. |

FOREIGN PATENT DOCUMENTS

| CN | 101389594 A | 3/2009 |
| CN | 102432473 A | 5/2012 |
| JP | 4118555 B2 | 7/2008 |
| WO | WO 2005/062724 A2 | 7/2005 |
| WO | WO 2006/076562 A1 | 7/2006 |
| WO | WO 2007/096124 A1 | 8/2007 |
| WO | WO 2008/040560 A1 | 4/2008 |
| WO | WO 2008/062472 A2 | 5/2008 |
| WO | WO 2009/057140 A2 | 5/2009 |
| WO | WO 2011/078101 A1 | 6/2011 |

OTHER PUBLICATIONS

International Search Report issued Mar. 11, 2014, in PCT/JP2014/050716, filed Jan. 16, 2014.
Plakhotnik, V. M., et al., Zhurnal Organicheskoi Khimii (1982), 18 (5), 1001-5.

*Primary Examiner* — Sudhakar Katakam
*Assistant Examiner* — Jennifer C Sawyer
(74) *Attorney, Agent, or Firm* — Oblon, McClelland, Maier & Neustadt, L.L.P.

(57) ABSTRACT

A method for manufacturing 3,5-dimethyl-1-adamantan-amine of the present invention comprises: (i) a step of reacting 3,5-dimethyl-1-adamantanol with an acid and nitrile in an organic solvent to obtain a reaction solution; (ii) a step of adding water to the reaction solution obtained in step (i) to obtain 1-amido-3,5-dimethyladamantane; and (iii) a step of hydrolyzing 1-amido-3,5-dimethyladamantane obtained in step (ii) in the presence of an alcohol-containing solvent and an inorganic base.

9 Claims, No Drawings

MANUFACTURING PROCESS FOR MEMANTINE

TECHNICAL FIELD

The present invention relates to a method for manufacturing 3,5-dimethyl-1-adamantanamine.

BACKGROUND ART 3,5-Dimethyl-1-adamantanamine (hereinafter, also described as "memantine") is a N-methyl-D-aspartate (hereinafter, also described as "NMDA") antagonist, and is used as an Alzheimer-type dementia therapeutic substance. The antagonist acts as a non-competitive electric dependent antagonist having low affinity for an NMDA receptor. Specifically, the antagonist is isolated from the NMDA receptor for transient highly-concentrated glutamate caused by physiological neuron excitation, and influences neither normal neural transmission nor long-term potentiation (LTP) formation. However, the antagonist protectively acts on neuron excitotoxicity for continuous low-concentrated glutamate stimulation. The antagonist has an action mechanism different from that of an acetylcholinesterase inhibitor, and therefore can also be used in combination with donepezil. Thus, the antagonist may extend the possibilities of Alzheimer-type dementia medical treatment.

As a method for synthesizing the antagonist, for example, various methods have been proposed as follows.

Non Patent Document 1 discloses a method for synthesizing 1-acetamido-3,5-dimethyladamantane involving reacting 3,5-dimethyl-1-adamantanol with acetonitrile and trifluoroacetic acid.

Patent Document 1 discloses a method for synthesizing aminoadamantanes. The method comprises:

(a1) a step of brominating adamantanes to synthesize bromoadamantanes, and thereafter hydrolyzing the bromoadamantanes to synthesize and isolate adamantanols;
(a2) a step of converting the adamantanols into acetamidoadamantanes; and (a3) a step of deacetylating the acetamidoadamantanes to obtain the aminoadamantanes.

Patent Document 2 discloses a method involving reacting adamantanes with an organic nitrile compound, concentrated sulfuric acid, and a carbocation compound in an organic solvent to synthesize 1-amidoadamantanes.

Patent Document 3 discloses a method for synthesizing memantine hydrochloride in which a stirring property is improved by using an organic acid for a solvent. The method comprises: (b1) a step of reacting 1-halo-3,5-dimethyladamantane with nitrile and concentrated sulfuric acid in an organic acid; (b2) a step of adding water to a reaction solution obtained in step (b1) to obtain 1-acetamido-3,5-dimethyladamantane as a crystal; (b3) a step of reacting 1-acetamido-3,5-dimethyladamantane obtained in step (b2) with a base in an alcohol; and (b4) a step of subjecting a reaction solution obtained in step (b3) to extraction, and thereafter adding hydrochloric acid to the resultant to obtain the memantine hydrochloride through crystallization.

Patent Document 4 discloses a method for synthesizing memantine hydrochloride in one pot. The method comprises: (c1) a step of reacting 1,3-dimethyladamantane with acetonitrile and an acid to synthesize 1-acetamido-3,5-dimethyladamantane; (c2) a step of reacting 1-acetamido-3,5-dimethyladamantane synthesized in step (c1) with a base in an alcohol solvent without isolating 1-acetamido-3,5-dimethyladamantane, to synthesize memantine; (c3) a step of adding hydrochloric acid dissolved in an alcohol solvent to the memantine obtained in step (c2); and (c4) a step of adding an ester solvent to the solution of step (c3) to obtain the memantine hydrochloride.

Patent Document 5 discloses a method for synthesizing memantine hydrochloride in one pot. The method comprises: (d1) a step of reacting 1-halo-3,5-dimethyladamantane with phosphoric acid and nitrile; and (d2) a step of synthesizing the memantine hydrochloride without isolating 1-acetamido-3,5-dimethyladamantane obtained in step (d1).

Patent Document 6 discloses a method for synthesizing memantine in one pot. The method comprises: (e1) a step of reacting 1-bromoadamantanes with acetamide and an inorganic acid in a solvent; (e2) a step of extracting 1-acetamidoadamantanes obtained in step (e1) by using an organic solvent; and (e3) a step of adding a base and diethylene glycol to a solution obtained in step (e2) to react them, to thereby obtain the memantine.

LIST OF PRIOR ART DOCUMENTS

Patent Document

Patent Document 1: International Publication No. WO 2005/062724
Patent Document 2: Japanese Patent No. 4118555
Patent Document 3: Chinese Patent No. 102432473
Patent Document 4: International Publication No. WO 2009/057140
Patent Document 5: International Publication No. WO 2006/076562
Patent Document 6: International Publication No. WO 2008/062472

Non Patent Document

Non Patent Document 1: Plakhotnik, V. M., Kovtun, V. Yu., Yashunskii, V. G., Zhurnal Organicheskoi Khimii (1982), 18(5), 1001-5

SUMMARY OF INVENTION

Problems to be Solved by Invention

However, the methods described in the above-mentioned prior art documents have the following problems.

The method described in Non Patent Document 1 uses 5 molar equivalent of acetonitrile and 8 molar equivalent of trifluoroacetic acid based on 3,5-dimethyl-1-adamantanol, which generates a large amount of waste.

The method described in Patent Document 1 uses 8 molar equivalent of poisonous bromine based on the adamantanes. The method uses 14 molar equivalent of acetonitrile and 28 molar equivalent of concentrated sulfuric acid based on the bromoadamantanes, which generates a large amount of waste.

The method described in Patent Document 2 uses 27 molar equivalent of concentrated sulfuric acid based on the adamantanes, which generates a large amount of waste.

The method described in Patent Document 3 uses poisonous halogen to synthesize 1-halo-3,5-dimethyladamantane. In addition, the method uses 15 molar equivalent of acetonitrile, 13 molar equivalent of concentrated sulfuric acid, and 21 molar equivalent of acetic acid based on 1-halo-3,5-dimethyladamantane in step (b1), which generates a large amount of waste.

The method described in Patent Document 4 uses 12 molar equivalent of acetonitrile and 24 molar equivalent of concentrated sulfuric acid based on 1,3-dimethyladamantane in step (c1), which generates a large amount of waste. In addition, 1-acetamido-3,5-dimethyladamantane obtained in step (c1) is extracted by using the organic solvent, and then subjected to solvent substitution with the alcohol solvent, which inefficiently causes an increase in the number of the steps.

The method described in Patent Document 5 uses poisonous halogen to synthesize 1-halo-3,5-dimethyladamantane. In addition, the method uses 5 molar equivalent of acetonitrile and 4 molar equivalent of phosphoric acid based on 1-halo-3,5-dimethyladamantane in step (d1), which generates a large amount of waste. 1-Acetamido-3,5-dimethyladamantane obtained in step (d1) is extracted by using 1-butanol, and then subjected to azeotropic dehydration, which inefficiently causes an increase in the number of the steps.

The method described in Patent Document 6 uses poisonous halogen to synthesize 1-bromoadamantanes. In addition, the method uses 6 molar equivalent of acetamide based on 1-bromoadamantanes in step (e1), which generates a large amount of waste. 1-Acetamidoadamantanes obtained in step (e1) is extracted by using toluene, and then subjected to solvent substitution with diethylene glycol by distilling off the toluene under reduced pressure, which inefficiently causes an increase in the number of the steps.

As described above, the conventional methods for synthesizing memantine have the following problems 1) to 3):

1) Excessive amounts of acid and nitrile are used over the adamantanes when 1-amido-3,5-dimethyladamantane is synthesized, which generates a large amount of waste derived from the acid and the nitrile;

2) When 1-halo-3,5-dimethyladamantane is synthesized, the poisonous halogen is used; and 3) 1-amido-3,5-dimethyladamantane is extracted by the organic solvent, and then subjected to solvent substitution with the alcohol solvent, which inefficiently causes an increase in the number of the steps.

Furthermore, the conventional methods for synthesizing memantine have the following problems 4) to 6):

4) Excessive amounts of acid and nitrile are used over the adamantanes when 1-amido-3,5-dimethyladamantane is synthesized, which causes an increase in a by-product to cause a decrease in a yield;

5) Heat generations such as reaction heats of nitrile and concentrated sulfuric acid or hydration heat of concentrated sulfuric acid when a reaction stops in addition to reaction heat when 1-amido-3,5-dimethyladamantane is synthesized cause a problem in safety during industrial operation; and 6) The reaction solution has a poor stirring property when 1-amido-3,5-dimethyladamantane is synthesized, which causes a decrease in a reaction rate to cause an increase in impurities, resulting in a decrease in a yield.

For this reason, there is desired a industrially safe, economical and efficient method for synthesizing memantine, which excludes a step of synthesizing 1-halo-3,5-dimethyladamantane using poisonous halogen; reduces the amounts of the acid and nitrile to be used relative to the amount of adamantanes in a synthesizing reaction of 1-amido-3,5-dimethyladamantane to increase the yield by suppressing a by-product and to largely reduce the waste derived from the acid and the nitrile; increases the yield by improving the stirring property of the reaction solution in the synthesizing reaction of 1-amido-3,5-dimethyladamantane; and does not need solvent substitution when a hydrolysis reaction is performed after the synthesizing reaction of 1-amido-3,5-dimethyladamantane.

Means for Solving Problems

The present inventors have conducted devoted examinations in view of this situation, and as a result, have found a method for manufacturing memantine having features shown below:

1) The amounts of an acid and nitrile to be used relative to the amount of adamantanes are largely reduced by using 3,5-dimethyl-1-adamantanol as a substrate in a synthesizing reaction of 1-amido-3,5-dimethyladamantane, which can suppress the generation of a by-product caused by using an excessive amount of reagent; allows heat to be easily removed when a synthesizing reaction of 1-amido-3,5-dimethyladamantane is terminated; and can largely reduce waste derived from the acid and the nitrile to reduce a cost and an environment load;

2) The stirring property of a reaction solution is improved without impairing the solubility of adamantanes to the reaction solution and the reactivity of adamantanes by performing the synthesizing reaction of 1-amido-3,5-dimethyladamantane in an organic solvent; and 3) After the end of the synthesizing reaction of 1-amido-3,5-dimethyladamantane, water is added to stop the reaction, and an alcohol solvent and an inorganic base are added to the obtained solution containing 1-amido-3,5-dimethyladamantane to hydrolyze 1-amido-3,5-dimethyladamantane to thereby obtain memantine without performing solvent substitution, which can provide simplification of the manufacturing step.

That is, the present invention is as follows.

[1] A method for manufacturing 3,5-dimethyl-1-adamantanamine comprising:
(i) a step of reacting 3,5-dimethyl-1-adamantanol with an acid and nitrile in an organic solvent to obtain a reaction solution;
(ii) a step of adding water to the reaction solution obtained in step (i) to obtain 1-amido-3,5-dimethyladamantane; and
(iii) a step of hydrolyzing 1-amido-3,5-dimethyladamantane obtained in step (ii) in the presence of an alcohol-containing solvent and an inorganic base.

[2] The method according to [1], wherein the organic solvent used in step (i) is hydrophobic.

[3] The method according to [1] or [2], wherein the organic solvent used in step (i) contains at least one organic solvent selected from the group consisting of an aliphatic hydrocarbon and an aromatic hydrocarbon.

[4] The method according to any of [1] to [3], wherein the alcohol-containing solvent used in step (iii) contains at least one alcohol selected from monovalent linear primary alcohols.

[5] The method according to any of [1] to [4], wherein the alcohol-containing solvent used in step (iii) contains at least one alcohol selected from the group consisting of 1-butanol, 1-pentanol, 1-hexanol, 1-heptanol, and 1-octanol.

[6] The method according to any of [1] to [5], wherein a molar ratio of the acid to 3,5-dimethyl-1-adamantanol in step (i) is 1 to 10.

[7] The method according to any of [1] to [6], wherein a molar ratio of the nitrile to 3,5-dimethyl-1-adamantanol in step (i) is 1 to 10.

[8] The method according to any of [1] to [7], wherein the acid used in step (i) contains at least one acid selected from the group consisting of sulfuric acid, nitric acid, phosphoric acid, trifluoroacetic acid, and toluenesulfonic acid.

[9] The method according to any of [1] to [8], wherein the acid used in step (i) contains concentrated sulfuric acid.

[10] The method according to any of [1] to [9], wherein the nitrile used in step (i) contains at least one nitrile selected from the group consisting of methane nitrile, acetonitrile, and propionitrile.

[11] The method according to any of [1] to [10], wherein the inorganic base used in step (iii) contains sodium hydrate or potassium hydrate.

Advantages of Invention

The present invention can provide a method for synthesizing memantine, which excludes a step of synthesizing 1-halo-3,5-dimethyladamantane using poisonous halogen; largely reduces the amounts of an acid and nitrile to be used relative to the amount of adamantanes in a synthesizing reaction of 1-amido-3,5-dimethyladamantane to increase a yield by suppressing a by-product and to largely reduce waste derived from the acid and the nitrile; increases the yield by improving the stirring property of a reaction solution when 1-amido-3,5-dimethyladamantane is synthesized; and can perform a hydrolysis reaction without performing solvent substitution after the synthesizing reaction of 1-amido-3,5-dimethyladamantane.

MODE FOR CARRYING OUT INVENTION

Hereinafter, an embodiment of the present invention (hereinafter, also described as "the present embodiment") will be described in detail. The following embodiment is illustrative in order to describe the present invention. The present invention is not limited only to the embodiment.

The present embodiment is represented by, for example, the following reaction formula (A). The present embodiment is a method for manufacturing 3,5-dimethyl-1-adamantanamine represented by the following formula 3. The method comprises: (i) a step of reacting 3,5-dimethyl-1-adamantanol (hereinafter, sometimes abbreviated to DMAO) represented by the following formula 1 with an acid and nitrile in an organic solvent to obtain a reaction solution; (ii) a step of adding water to the reaction solution obtained in step (i) to obtain 1-amido-3,5-dimethyladamantane (hereinafter, sometimes abbreviated to AMDA) represented by the following formula 2; and (iii) a step of hydrolyzing 1-amido-3,5-dimethyladamantane obtained in step (ii) in the presence of an alcohol-containing solvent and an inorganic base.

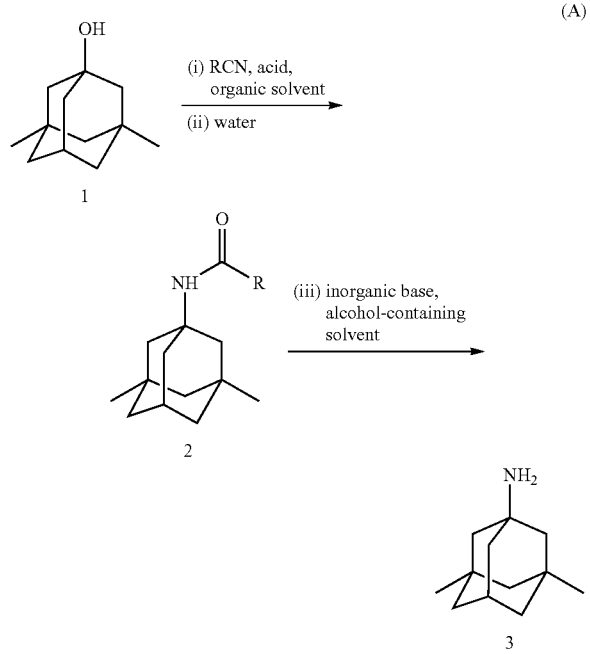

<Step (i)>

In step (i), preferably, 3,5-dimethyl-1-adamantanol represented by the formula 1 and nitrile are dissolved in an organic solvent to obtain a solution, and an acid is added to the obtained solution to allow to react to thereby obtain a reaction solution. Next, in step (ii) described below, water is added to the reaction solution obtained in step (i) to generate 1-amido-3,5-dimethyladamantane represented by the formula 2.

3,5-Dimethyl-1-adamantanol which is available industrially or as a reagent can be used as a raw material without being limited at all. The manufacturing method is not particularly limited and, for example, air oxidation of 1,3-dimethyladamantane is known. Specifically, 3,5-dimethyl-1-adamantanol can be obtained according to a method described in Journal of the American Chemical Society; vol. 122; 30; (2000); p.7390-7391 using 1,3-dimethyladamantane as a raw material, but are not particularly limited thereto. Use of the raw material obtained by this manufacturing method can avoid use of poisonous halide, which is suitable also from a safety aspect and an environment aspect.

Specific examples of the acid used in step (i) include, but are not particularly limited to, sulfuric acid, nitric acid, hydrochloric acid, phosphoric acid, trifluoroacetic acid, methanesulfonic acid, benzenesulfonic acid, toluenesulfonic acid, or trifluoromethanesulfonic acid. These acids may be used in the form of a mixture of two or more thereof. Particularly, at least one selected from the group consisting of sulfuric acid, nitric acid, phosphoric acid, trifluoroacetic acid, and toluenesulfonic acid is preferably contained in the acid used in step (i), and concentrated sulfuric acid is more preferably contained. A reaction rate tends to be improved by using the acid, which is preferable.

In step (i), the molar ratio of the acid to 3,5-dimethyl-1-adamantanol is preferably 1 to 10, more preferably 2 to 5, and still more preferably 2 to 3. In step (i), when the amount of the acid to be used is equal to or less than the above-mentioned upper limit, a by-product can be suppressed to improve a yield, and waste derived from the acid can be largely reduced. In addition, the amount of the acid to be used is economical. When the amount of the acid to be used is equal to or more than the above-mentioned lower limit, the reaction tends to sufficiently proceed and be completed.

R of nitrile (RCN) used in step (i) may be hydrogen, an alkyl group, an aryl group, or an aralkyl group. Specifically, the alkyl group is preferably an alkyl group having 1 to 6 carbon atoms such as a methyl group, an ethyl group, or a propyl group. The aryl group is preferably an aryl group having 6 to 10 carbon atoms such as a phenyl group. The aralkyl group is preferably an aralkyl group having 7 to 12 carbon atoms such as a benzyl group.

Specific examples of the nitrile used in step (i) include, but are not particularly limited to, methane nitrile, acetonitrile, propionitrile, benzylnitrile, and vinylacetonitrile. The nitrile used in step (i) preferably contains at least one nitrile selected from the group consisting of methane nitrile, acetonitrile, and propionitrile, and more preferably contains acetonitrile. The amount of waste derived from the nitrile can be reduced by using such a nitrile, which is preferable.

Since the reaction between 3,5-dimethyl-1-adamantanol and the nitrile is a stoichiometric reaction in step (i), the amount of the nitrile to be used is preferably equal to or greater than 1 molar equivalent based on 1 mol of 3,5-dimethyl-1-adamantanol. In step (i), the molar ratio of the nitrile to 3,5-dimethyl-1-adamantanol is preferably 1 to 10, more preferably 1 to 4, and still more preferably 1 to 2. When the amount of the nitrile to be used is equal to or less than the above-mentioned upper limit in step (i), a by-product can be suppressed to improve a yield, and the waste derived from the nitrile can be reduced.

In step (i), use of the organic solvent can prevent an increase in a viscosity and a poor stirring property of the reaction solution, and can remove heat. As the organic solvent, an organic solvent which can be separated from water, does not inhibit the reaction, and dissolves 3,5-dimethyl-1-adamantanol and 1-amido-3,5-dimethyladamantane can be used without being limited at all. However, the nitrile involved in the reaction of step (i) is excluded as the organic solvent used for step (i).

Specific examples of the organic solvent which can be used in step (i) include, but are not particularly limited to, halogenated aliphatic hydrocarbons such as methylene chloride, chloroform, and carbon tetrachloride; aliphatic hydrocarbons such as hexane and heptane; halogenated aromatic hydrocarbons such as chlorobenzene; aromatic hydrocarbons such as benzene, toluene, xylene, and mesitylene; ethers such as diisopropyl ether and 1,4-dioxane; esters such as ethyl acetate, propyl acetate, and butyl acetate; and carbonates such as dimethyl carbonate. The organic solvent used in step (i) is preferably at least one selected from the aliphatic hydrocarbon, the aromatic hydrocarbon, and the ethers. The organic solvent used in step (i) is more preferably hydrophobic, and still more preferably contains at least one organic solvent selected from the group consisting of the aliphatic hydrocarbon and the aromatic hydrocarbon. As the organic solvent used in step (i), there are particularly preferably aromatic hydrocarbons such as toluene and xylene, which have a high boiling point and are easily used as a mixed solvent with an alcohol solvent during a hydrolysis reaction of 1-amido-3,5-dimethyladamantane of step (iii) described below. Among them, use of toluene as the organic solvent used in step (i) provides an improvement in the yield of 1-amido-3,5-dimethyladamantane, and makes it unnecessary to perform solvent substitution before the hydrolysis reaction of step (iii) described below, which can provide simplification of the manufacturing step.

In step (i), the organic solvents may be used singly or in combinations of two or more.

In step (i), the amount of the organic solvent to be used is not particularly limited, and is preferably 1 to 50 times by weight, more preferably 1 to 20 times by weight, and still more preferably 1 to 3 times by weight based on the amount of 3,5-dimethyl-1-adamantanol. The amount of the organic solvent to be used within the above-mentioned range economically provides a sufficient yield per unit capacity of one batch without causing an excessive amount of the organic solvent and provides improvements in a stirring property and heat removal of the reaction solution without causing an inadequate amount of the organic solvent, which is preferable.

A reaction temperature in step (i) is not particularly limited, and is preferably in a range of 0° C. to 100° C., and more preferably 0° C. to 70° C. The reaction temperature in step (i) within the above-mentioned range suppresses a by-product without causing a too high temperature, and provides a suitable reaction rate without causing a too low temperature.

A reaction time in step (i) is not also particularly limited. The reaction time is changed depending on the amounts of the acid, nitrile, and organic solvent to be used, and cannot make a generalization. It is ordinarily sufficient when the reaction time is 2 to 24 hours.

<Step (ii)>

Step (ii) is a step of adding water to the reaction solution obtained in step (i) to obtain 1-amido-3,5-dimethyladamantane. 1-Amido-3,5-dimethyladamantane obtained in step (ii) is preferably the compound represented by the formula 2. R in the formula 2 has the same meaning as that of R of the above-mentioned nitrile (RCN).

In step (ii), the amount of the water to be added is preferably 3 to 10 times by weight, more preferably 3 to 5 times by weight, and still more preferably 3 to 4 times by weight based on the amount of the acid to be used in step (1). The amount of the water to be added within the above-mentioned range economically provides a suitable yield per unit capacity of one batch without causing an excessive amount of the water, and provides an improvement in a liquid separation property without causing an inadequate amount of the water, which is preferable.

<Step (iii)>

Step (iii) is a step of hydrolyzing 1-amido-3,5-dimethyladamantane obtained in step (ii) in the presence of an alcohol-containing solvent and an inorganic base.

Specifically, in step (iii), for example, a mixed solvent solution of 1-amido-3,5-dimethyladamantane can be obtained by adding an alcohol solvent to the reaction solution obtained in step (ii) and thereafter separating an aqueous phase. As another specific example, for example, the mixed solvent solution of 1-amido-3,5-dimethyladamantane can be obtained by separating the aqueous phase of the reaction solution obtained in step (ii), and thereafter adding an alcohol solvent to the obtained organic phase.

Then, for example, an inorganic base is added to the obtained mixed solvent solution to hydrolyze 1-amido-3,5-dimethyladamantane, and thereby memantine represented by the formula 3 can be obtained. As another specific example, for example, memantine represented by the formula 3 can also be obtained by hydrolyzing 1-amido-3,5-dimethyladamantane isolated from the obtained organic phase and represented by the formula 2 in the presence of an inorganic base and an alcohol solvent. The hydrolysis reaction can be carried out under increased pressure using an autoclave even when the alcohol-containing solvent to be used has a low boiling point.

The alcohol-containing solvent used in step (iii) is not particularly limited, as long as it contains the alcohol solvent. The alcohol-containing solvent is preferably a mixed solvent of the organic solvent used in step (i) and the alcohol solvent. Such an alcohol-containing solvent makes it unnecessary to perform solvent substitution before the hydrolysis reaction of step (iii), which can provide simplification of the manufacturing step.

Specific examples of the kinds of the alcohol solvent which can be used in step (iii) include, but are not particularly limited to, a monovalent alcohol solvent having 1 to 10 carbon atoms such as methanol, ethanol, 1-propanol, 2-propanol, 1-butanol, 2-butanol, 1-pentanol, 2-pentanol, 1-hexanol, 1-heptanol, 1-octanol, cyclohexanol, or 2-ethyl-1-hexanol; and a divalent alcohol solvent having 2 to 10 carbon atoms such as ethylene glycol or propylene glycol. The alcohol solvent used in step (iii) is preferably a monovalent linear primary alcohol such as 1-butanol, 1-pentanol, 1-hexanol, 1-heptanol, or 1-octanol. Particularly, when the alcohol-containing solvent used in step (iii) is a mixed solvent of a linear primary alcohol and toluene, the yield of memantine obtained by the hydrolysis of step (iii) is dramatically improved.

Also in step (iii), the alcohol solvents may be used singly or in combinations of two or more.

In step (iii), the amount of the alcohol solvent to be used is preferably 0.5 to 10 times by weight, more preferably 1.0 to 5.0 times by weight, and still more preferably 1.0 to 2.0 times by weight based on the amount of the organic solvent to be used in step (i). In step (iii), the amount of the alcohol solvent to be used equal to or less than the above-mentioned upper limit economically provides an increase in a yield per unit capacity of one batch. The amount of the alcohol solvent to be used equal to or more than the above-mentioned lower limit tends to provide an improvement in the operability of the reaction solution.

When liquid separation operation is performed to separate the organic phase and the aqueous phase from each other in step (iii), the number of the liquid separation operations is preferably 2 to 5 times, and more preferably 2 to 3 times. When the number of the liquid separation operations is set to the above-mentioned range, the number is economical, and the acid can be sufficiently washed, which is preferable.

Specific examples of the inorganic base used in step (iii) include, but are not particularly limited to, lithium hydrate, sodium hydrate, potassium hydrate, and cesium hydrate. The inorganic base used in step (iii) is preferably sodium hydrate or potassium hydrate.

In step (iii), the amount of the inorganic base to be used is preferably 4 to 20 molar equivalent, and more preferably 4 to 10 molar equivalent based on 1-amido-3,5-dimethyladamantane. When the amount of the inorganic base to be used is set to the above-mentioned range, the amount is economical, and the reaction rate is suitable, which is preferable.

A reaction temperature in step (iii) is preferably in a range of 100° C. to 160° C., and more preferably in a range of 120° C. to 140° C. The reaction temperature in step (iii) within the above-mentioned range suppresses a by-product without causing a too high temperature, and provides a suitable reaction rate without causing a too low temperature, which is preferable.

A reaction time in step (iii) is changed depending on the amounts of the inorganic base, organic solvent, and alcohol solvent to be used, and cannot make a generalization. The reaction time is preferably 18 to 30 hours, and more preferably 18 to 24 hours.

<Other Steps>

Next, a manufacturing method of the present embodiment preferably comprises step (iv) of adding water to the reaction solution obtained in the hydrolysis reaction of step (iii), and thereafter separating an aqueous phase by liquid separation operation to obtain a memantine solution.

In step (iv), the amount of the water to be added to the reaction solution obtained in the hydrolysis reaction of step (iii) is preferably 0.5 to 10 times by weight, more preferably 0.5 to 5.0 times by weight, and still more preferably 0.5 to 2.0 times by weight based on the amount of the reaction solution. In step (iv), the amount of the water to be used within the above-mentioned range economically provides a suitable yield per unit capacity of one batch without causing an excessive amount of the water, and provides an improvement in a liquid separation property without causing an inadequate amount of the water, which is preferable.

In step (iv), it is suitable that the number of the liquid separation operations be 2 to 5 times, and preferably 2 to 3 times. The range is economical, and can provide sufficient washing of sodium hydrate, which is preferable.

The manufacturing method of the present embodiment preferably comprises step (v) of adding hydrochloric acid to the memantine solution obtained in step (iv) to obtain memantine hydrochloride. A method for isolating and purifying the memantine hydrochloride obtained in step (v) is not particularly limited, and a known method is employed. For example, the memantine hydrochloride can be isolated and purified by filtering or centrifuging a crystal deposited after a solution containing the memantine hydrochloride obtained in step (v) is concentrated. It is preferable to concentrate the solution containing the memantine hydrochloride obtained in step (v), then to add a poor solvent thereto in order to perform crystallization, and to filter the deposited crystal, to thereby suitably isolated and purified the memantine hydrochloride.

EXAMPLES

Next, the present invention will be specifically described with reference to Examples and Comparative Examples. However, the present invention is not limited by these Examples.

Reaction tracing and analysis of memantine hydrochloride product were performed under analysis conditions shown below. Analysis device: SHIMADZU GC-2014, column: TC-1701 (30 m×0.25 mm I. D., 0.50 μm film), carrier gas: He, 1.61 mL/min, inlet: 180° C. (split 1:50), detector: FID, 280° C., oven: 80° C. (5 minutes) to 20° C./minute to 280° C. (5 minutes), amount of injection: 1.0 μL Example 1

10.00 g (55.5 mmol) of 3,5-dimethyl-1-adamantanol, 4.55 g (110.9 mmol) of acetonitrile, and 25.00 g of toluene were added to a 300 mL round-bottom flask to obtain a mixed solution. 3,5-Dimethyl-1-adamantanol was manufactured according to a method described in p.7390-7391 of Journal of the American Chemical Society (vol. 122, 30, 2000). Next, 11.00 g (108.8 mmol) of 97% concentrated sulfuric acid was dropped into the mixed solution in the flask over 23 minutes to obtain a reaction solution. The obtained reaction solution was stirred at 21° C. for 2 hours to continue the reaction. In the reaction solution, the disappearance of 3,5-dimethyl-1-adamantanol was confirmed by gas chromatography (GC), and the reaction was then stopped by adding 33.66 g of water to the reaction solution to obtain a toluene solution containing 1-acetamido-3,5-dimethyladamantane (two-phase solution). 25.01 g of 1-hexanol was added to the two-phase solution, and liquid separation operation was performed twice. An aqueous phase was removed from the two-phase solution to obtain a solution containing 1-acetamido-3,5-dimethyladamantane. 8.71 g (217.75 mmol) of sodium hydrate was added to the obtained solution to obtain a reaction solution. The obtained reaction solution was stirred at 126° C. for 18 hours to hydrolyze 1-acetamido-3,5-dimethyladamantane. In the reaction solution, the disappearance of 1-acetamido-3,5-dimethyladamantane and the generation of memantine were confirmed by GC, and the reaction was then stopped by adding 67.21 g of water to the reaction solution to obtain a solution containing memantine. Then, liquid separation operation of the obtained solution was performed 3 times, and an aqueous phase was separated from the solution to obtain a solution containing memantine. 5.61 g (56.93 mmol) of 37% hydrochloric acid was added to the obtained solution containing memantine to form memantine hydrochloride. Then, the solution containing memantine hydrochloride was concentrated. 224.40 g of ethyl acetate was added to 56.10 g of the concentrated solution to perform crystallization at 20° C. The deposited crystal was filtered, and the obtained filtered product was then washed with 40.00 g of ethyl acetate 3 times. After washing, the obtained crystal was vacuum-dried at 60° C. for 6 hours to obtain 10.45 g of memantine hydrochloride as a colorless crystal (yield: 87.3%, GC purity: 100.0%).

Example 2

1.00 g (5.50 mmol) of 3,5-dimethyl-1-adamantanol, 0.46 g (11.1 mmol) of acetonitrile, and 9.61 g of mesitylene were added to a test tube having an outer diameter of 30 mm to obtain a mixed solution. Then, 1.12 g (11.1 mmol) of 97% concentrated sulfuric acid was dropped into the mixed solution in the test tube to obtain a reaction solution. The obtained reaction solution was stirred at 30° C. for 3 hours to continue the reaction. Then, 6.09 g of water was added to the reaction solution to stop the reaction, and an aqueous phase was removed by washing from the reaction solution to obtain a mesitylene solution containing 1-acetamido-3,5-dimethyladamantane (reaction yield: 80.4%). Then, 0.71 g of sodium hydrate (NaOH) and 9.61 g of 1-hexanol were added to the obtained solution to obtain a reaction solution. The obtained reaction solution was stirred at 130° C. for 18 hours to hydrolyze 1-acetamido-3,5-dimethyladamantane. Then, in the reaction solution, the generation of memantine was confirmed by GC (reaction yield: 96.2%).

Example 3

0.09 g (0.50 mmol) of 3,5-dimethyl-1-adamantanol, 0.25 g (6.0 mmol) of acetonitrile, and 0.87 g of toluene were added to a test tube having an outer diameter of 15 mm to obtain a mixed solution. Then, 0.19 g (1.00 mmol) of para-toluenesulfonic acid was added to the mixed solution in the test tube to obtain a reaction solution. The obtained reaction solution was stirred at 70° C. for 24 hours to continue the reaction. Then, 1.00 g of water was added to the reaction solution to stop the reaction. An aqueous phase was removed by washing from the reaction solution to obtain a toluene solution containing 1-acetamido-3,5-dimethyladamantane (reaction yield: 64%). Then, 0.052 g of sodium hydrate (NaOH) and 0.82 g of 1-hexanol were added to the obtained solution to obtain a reaction solution. The obtained reaction solution was stirred at 126° C. for 18 hours to hydrolyze 1-acetamido-3,5-dimethyladamantane. Then, in the reaction solution, the generation of memantine was confirmed by GC (reaction yield: 96%).

Examples 4 to 11

A toluene solution containing 1-acetamido-3,5-dimethyladamantane obtained by the same method as that of Example 1 was washed by using water. Then, 0.28 g (1.3 mmol) of 1-acetamido-3,5-dimethyladamantane (substrate) and 0.69 g of toluene were fractionated to a test tube having an outer diameter of 15 mm from the solution to obtain the toluene solution containing 1-acetamido-3,5-dimethyladamantane. 0.20 g (5.0 mmol) of sodium hydrate and 0.69 g of each alcohol solvent shown in Table 1 were added to the obtained solution to obtain a reaction solution. The obtained reaction solution was stirred under a solvent reflux condition for 24 hours to hydrolyze 1-acetamido-3,5-dimethyladamantane. Then, the reaction solution was analyzed by using GC. The results were shown in Table 1.

TABLE 1

| | | GC-Area [%] of each component in reaction solution | | |
|---|---|---|---|---|
| Examples | alcohol solvent | substrate | memantine | by-product |
| 4 | 1-butanol | 1 | 99 | 0 |
| 5 | 1-pentanol | 0 | 100 | 0 |
| 6 | 1-hexanol | 0 | 100 | 0 |
| 7 | 1-heptanol | 0 | 100 | 0 |
| 8 | 1-octanol | 0 | 100 | 0 |
| 9 | ethylene glycol | 97 | 3 | 0 |
| 10 | cyclohexanol | 43 | 55 | 2 |
| 11 | 2-ethyl-1-hexanol | 4 | 96 | 1 |

Examples 12 to 20

1-Acetamido-3,5-dimethyladamantane was isolated from a toluene solution containing 0.28 g (1.3 mmol) of 1-acetamido-3,5-dimethyladamantane obtained by the same method as that of Example 1. In a test tube having an outer diameter of 15 mm, a solvent having a weight ratio shown in Table 2 was added to the obtained 1-acetamido-3,5-dimethyladamantane to obtain a solution. 0.20 g (5.00 mmol) of sodium hydrate was added to (2.77 g of) the obtained solution to obtain a reaction solution. The reaction solution was heated at each solution temperature shown in Table 2, and stirred for 24 hours to hydrolyze 1-acetamido-3,5-dimethyladamantane. Then, the reaction solution was analyzed by using GC. The reaction yield was obtained by an absolute calibration method using a standard preparation. The results were shown in Table 2.

TABLE 2

| Examples | solvent (weight ratio: toluene/1-hexanol) | solution temperature [° C.] | reaction yield [%] |
|---|---|---|---|
| 12 | 0/100 | 135 | 101.2 |
| 13 | 10/90 | 134 | 102.2 |
| 14 | 20/80 | 133 | 104.7 |
| 15 | 30/70 | 130 | 97.1 |
| 16 | 40/60 | 126 | 102.7 |
| 17 | 50/50 | 120 | 100.8 |
| 18 | 60/40 | 118 | 98.2 |
| 19 | 70/30 | 116 | 89.8 |
| 20 | 80/20 | 115 | 72.8 |

Comparative Example 1

0.090 g (0.50 mmol) of 3,5-dimethyl-1-adamantanol and 0.041 g (1.00 mmol) of acetonitrile were added to a test tube having an outer diameter of 15 mm to obtain a mixed solution. Then, 0.10 g (1.00 mmol) of 97% sulfuric acid was added to the mixed solution in the test tube to obtain a reaction solution. When the obtained reaction solution was stirred at 70° C. for 3 hours, a reactant was solidified, which caused difficult stirring.

Examples 21 to 42 and Comparative Examples 2 and 3

An aqueous phase was removed from a toluene solution containing 1-acetamido-3,5-dimethyladamantane obtained by the same method as that of Example 1, to obtain an organic phase. Next, in a test tube having an outer diameter of 15 mm, an alcohol solvent or the like was added to the obtained organic phase containing 1-acetamido-3,5-dimethyladamantane (substrate) so that each substrate concentration shown in Table 3 was set, to obtain a solution. An inorganic base was added to the obtained solution as shown in Table 3 to obtain a reaction solution. The obtained reaction solution was refluxed at each reaction temperature shown in Table 3 for 24 hours to hydrolyze 1-acetamido-3,5-dimethyladamantane. Then, the reaction solution was analyzed by using GC. The results were shown in Table 3.

TABLE 3

|  | inorganic base | | alcohol solvent or the like | | | GC-Area (%) in reaction solution | | |
|---|---|---|---|---|---|---|---|---|
|  | kind | molar equivalent based on substrate | kind | substrate concentration (g/mL) | reaction temperature (° C.) | substrate | memantine | other |
| Example 21 | NaOH | 8.0 | n-BuOH | 0.167 | 116(reflux) | 4 | 96 | 0 |
| Example 22 | NaOH | 6.0 | n-BuOH | 0.167 | 116(reflux) | 2 | 96 | 2 |
| Example 23 | NaOH | 4.0 | n-BuOH | 0.167 | 116(reflux) | 4 | 95 | 0 |
| Example 24 | NaOH | 2.0 | n-BuOH | 0.167 | 116(reflux) | 16 | 84 | 1 |
| Example 25 | NaOH | 10.0 | n-BuOH | 0.083 | 116(reflux) | 0 | 98 | 2 |
| Example 26 | NaOH | 10.0 | n-BuOH | 0.063 | 116(reflux) | 0 | 97 | 3 |
| Example 27 | NaOH | 10.0 | n-BuOH | 0.042 | 116(reflux) | 3 | 97 | 0 |
| Example 28 | KOH | 10.0 | n-BuOH | 0.083 | 116(reflux) | 20 | 80 | 0 |
| Example 29 | NaOH | 10.0 | i-BuOH | 0.083 | 108(reflux) | 3 | 95 | 2 |
| Comparative Example 2 | NaOH | 10.0 | 1,4-dioxane | 0.083 | 102(reflux) | 100 | 0 | 0 |
| Comparative Example 3 | NaOH | 10.0 | toluene | 0.083 | 111(reflux) | 100 | 0 | 0 |
| Example 30 | NaOH | 10.0 | i-Pentanol | 0.083 | 132(reflux) | 0 | 91 | 9 |
| Example 31 | NaOH | 8.0 | i-Pentanol | 0.083 | 132(reflux) | 0 | 75 | 25 |
| Example 32 | NaOH | 6.0 | i-Pentanol | 0.083 | 132(reflux) | 0 | 83 | 17 |
| Example 33 | NaOH | 4.0 | i-Pentanol | 0.083 | 132(reflux) | 0 | 70 | 30 |
| Example 34 | NaOH | 2.0 | i-Pentanol | 0.083 | 132(reflux) | 12 | 85 | 3 |
| Example 35 | NaOH | 10.0 | n-Pentanol | 0.083 | 138(reflux) | 0 | 99 | 1 |
| Example 36 | NaOH | 8.0 | n-Pentanol | 0.083 | 138(reflux) | 0 | 99 | 1 |
| Example 37 | NaOH | 6.0 | n-Pentanol | 0.083 | 138(reflux) | 0 | 99 | 1 |
| Example 38 | NaOH | 4.0 | n-Pentanol | 0.083 | 138(reflux) | 0 | 98 | 2 |
| Example 39 | NaOH | 2.0 | n-Pentanol | 0.083 | 138(reflux) | 9 | 88 | 3 |
| Example 40 | NaOH | 3.0 | n-Pentanol | 0.083 | 138(reflux) | 1 | 96 | 4 |
| Example 41 | NaOH | 2.0 | n-Pentanol | 0.167 | 138(reflux) | 5 | 94 | 2 |
| Example 42 | NaOH | 2.0 | n-Pentanol | 0.111 | 138(reflux) | 5 | 93 | 2 |

Examples 43 to 54

An aqueous phase was removed from a toluene solution containing 1-acetamido-3,5-dimethyladamantane obtained by the same method as that of Example 1, to obtain an organic phase. Next, in a test tube having an outer diameter of 15 mm, an alcohol solvent was added to the obtained organic phase containing 1-acetamido-3,5-dimethyladamantane (substrate) so that a substrate concentration shown in Table 4 was set, to obtain a solution. An inorganic base was added to the obtained solution as shown in Table 4 to obtain a reaction solution. The obtained reaction solution was heated at each reaction temperature shown in Table 3 for 24 hours to hydrolyze 1-acetamido-3,5-dimethyladamantane. Then, the reaction solution was analyzed by using GC. The results were shown in Table 4.

TABLE 4

|  | inorganic base | | alcohol solvent or the like | | | GC-Area (%) in reaction solution | | |
|---|---|---|---|---|---|---|---|---|
|  | kind | molar equivalent based on substrate | kind | substrate concentration (g/mL) | reaction temperature (° C.) | substrate | memantine | other |
| Example 43 | NaOH | 10.0 | n-Pentanol | 0.083 | 120 | 0 | 100 | 0 |
| Example 44 | NaOH | 10.0 | i-Pentanol | 0.083 | 120 | 0 | 93 | 7 |
| Example 45 | NaOH | 4.0 | n-Hexanol | 0.083 | 140 | 0 | 96 | 4 |
| Example 46 | NaOH | 4.0 | n-Heptanol | 0.083 | 140 | 0 | 99 | 1 |
| Example 47 | NaOH | 4.0 | Cyclohexanol | 0.083 | 140 | 10 | 89 | 1 |
| Example 48 | NaOH | 4.0 | 2-Et-hexanol | 0.083 | 140 | 4 | 77 | 19 |
| Example 49 | NaOH | 4.0 | EG | 0.083 | 140 | 24 | 74 | 3 |

TABLE 4-continued

|  | inorganic base | | alcohol solvent or the like | | | GC-Area (%) in reaction solution | | |
|---|---|---|---|---|---|---|---|---|
|  | | molar equivalent based on | | substrate concentration | reaction temperature | | | |
|  | kind | substrate | kind | (g/mL) | (° C.) | substrate | memantine | other |
| Example 50 | NaOH | 10.0 | EG | 0.083 | 140 | 2 | 92 | 6 |
| Example 51 | NaOH | 4.0 | EG | 0.167 | 140 | 10 | 89 | 1 |
| Example 52 | NaOH | 10.0 | EG | 0.167 | 140 | 27 | 72 | 1 |
| Example 53 | NaOH | 10.0 | EG | 0.250 | 140 | 20 | 78 | 2 |
| Example 54 | NaOH | 10.0 | EG | 0.333 | 140 | 17 | 81 | 2 |

Reference Examples 1 to 3

0.09 g (0.5 mmol) of 3,5-dimethyl-1-adamantanol, 0.04 g (1 mmol) of acetonitrile, and 1.0 mL of each kind of organic solvent shown in Table 5 were added to a test tube having an outer diameter of 15 mm to obtain a mixed solution. 3,5-Dimethyl-1-adamantanol was manufactured according to a method described in p.7390-7391 of Journal of the American Chemical Society (vol. 122, 30, 2000). Next, 0.1 g (1 mmol) of 97% concentrated sulfuric acid was dropped into the mixed solution in the test tube to obtain a reaction solution. The obtained reaction solution was stirred at 70° C. for 24 hours to continue the reaction. Then, the reaction solution was analyzed by using GC. The results were shown in Table 5.

TABLE 5

| Reference Examples | organic solvent | GC-Area (%) in reaction solution | | |
|---|---|---|---|---|
|  |  | raw material | subject matter | other |
| 1 | 1,2-dichloroethane | 0 | 96 | 4 |
| 2 | toluene | 0 | 91 | 9 |
| 3 | dioxane | 64 | 32 | 4 | target compound: 1-acetamido-3,5-dimethyladamantane
starting material: 3,5-dimethyl-1-adamantanol Reference Examples 4 to 33

Acetonitrile was added at each molar equivalent as shown in Table 6 based on 3,5-dimethyl-1-adamantanol to a test tube having an outer diameter of 15 mm. Furthermore, each organic solvent of times by weight shown in Table 6 was added to the test tube to obtain a mixed solution. 3,5-Dimethyl-1-adamantanol was manufactured according to a method described in p.7390-7391 of Journal of the American Chemical Society (vol. 122, 30, 2000). Next, as shown in Table 6, sulfuric acid was dropped into the mixed solution in the test tube to obtain a reaction solution, and the obtained reaction solution was stirred at each reaction temperature for each reaction time as shown in Table 6 to continue the reaction. Then, the reaction solution was analyzed by using GC. The results were shown in Table 6.

TABLE 6

|  | sulfuric acid | | acetonitrile | organic solvent | | | | GC-Area (%) in reaction solution | | | | reaction |
|---|---|---|---|---|---|---|---|---|---|---|---|---|
|  | concentration [%] | molar equivalent based on DMAO | molar equivalent based on DMAO | kind | amount in terms of times by weight based on DMAO | reaction temperature [° C.] | reaction time [h] | DMAO | ADMA | DMA-tol | other | yield [%] |
| Reference Example 4 | 97 | 2.0 | 2.0 | toluene | 9.6 | 70 | 3.5 | 3 | 93 | 4 | 1 | 78.2 |
| Reference Example 5 | 97 | 2.0 | 2.0 | toluene | 9.6 | 20 | 3.5 | 1 | 96 | 1 | 2 | 82.2 |
| Reference Example 6 | 97 | 2.0 | 2.0 | mesitylene | 9.6 | 30 | 3 | 1 | 98 | 0 | 2 | 80.4 |
| Reference Example 7 | 97 | 2.0 | 2.0 | toluene | 9.6 | 30 | 24 | 0 | 98 | 1 | 1 | 80.7 |
| Reference Example 8 | 90 | 2.0 | 2.0 | toluene | 9.6 | 30 | 24 | 2 | 96 | 0 | 2 | 77.6 |
| Reference Example 9 | 80 | 2.0 | 2.0 | toluene | 9.6 | 30 | 24 | 22 | 73 | 0 | 5 | 49.3 |
| Reference Example 10 | 70 | 2.0 | 2.0 | toluene | 9.6 | 30 | 24 | 62 | 28 | 0 | 10 | 18.6 |
| Reference Example 11 | 60 | 2.0 | 2.0 | toluene | 9.6 | 30 | 24 | 87 | 6 | 0 | 7 | 2.2 |
| Reference Example 12 | 97 | 1.0 | 2.0 | toluene | 9.6 | 30 | 3 | 75 | 15 | 1 | 9 | 11.0 |

TABLE 6-continued

|  | sulfuric acid | acetonitrile | organic solvent | | | | GC-Area (%) in reaction solution | | | | reaction |
|---|---|---|---|---|---|---|---|---|---|---|---|
|  | concentration [%] | molar equivalent based on DMAO | molar equivalent based on DMAO | kind | amount in terms of times by weight based on DMAO | reaction temperature [°C.] | reaction time [h] | DMAO | ADMA | DMA-tol | other | yield [%] |
| Reference Example 13 | 97 | 2.0 | 2.0 | toluene | 9.6 | 30 | 3 | 0 | 96 | 1 | 2 | 81.9 |
| Reference Example 14 | 97 | 4.0 | 2.0 | toluene | 9.6 | 30 | 3 | 0 | 45 | 49 | 5 | 43.1 |
| Reference Example 15 | 97 | 6.0 | 2.0 | toluene | 9.6 | 30 | 3 | 0 | 7 | 88 | 5 | 8.5 |
| Reference Example 16 | 97 | 8.0 | 2.0 | toluene | 9.6 | 30 | 3 | 0 | 5 | 91 | 4 | 6.0 |
| Reference Example 17 | 97 | 2.0 | 1.0 | toluene | 9.6 | 30 | 3 | 0 | 94 | 3 | 3 | 79.5 |
| Reference Example 18 | 97 | 2.0 | 2.0 | toluene | 9.6 | 30 | 3 | 0 | 97 | 1 | 2 | 84.6 |
| Reference Example 19 | 97 | 2.0 | 4.0 | toluene | 9.6 | 30 | 3 | 0 | 98 | 1 | 1 | 80.1 |
| Reference Example 20 | 97 | 2.0 | 6.0 | toluene | 9.6 | 30 | 3 | 1 | 97 | 0 | 1 | 80.2 |
| Reference Example 21 | 97 | 2.0 | 8.0 | toluene | 9.6 | 30 | 3 | 4 | 95 | 0 | 1 | 77.4 |
| Reference Example 22 | 97 | 2.0 | 2.0 | toluene | 2.0 | 30 | 3 | 1 | 96 | 2 | 2 | 79.1 |
| Reference Example 23 | 97 | 2.0 | 2.0 | toluene | 4.0 | 30 | 3 | 0 | 96 | 2 | 2 | 80.8 |
| Reference Example 24 | 97 | 2.0 | 2.0 | toluene | 6.0 | 30 | 3 | 0 | 96 | 2 | 3 | 80.7 |
| Reference Example 25 | 97 | 2.0 | 2.0 | toluene | 8.0 | 30 | 3 | 0 | 96 | 2 | 2 | 81.1 |
| Reference Example 26 | 97 | 2.0 | 2.0 | toluene | 9.6 | 30 | 3 | 0 | 95 | 2 | 3 | 79.0 |
| Reference Example 27 | 97 | 2.0 | 2.0 | toluene | 9.6 | 30 | 3 | 0 | 96 | 2 | 2 | 80.5 |
| Reference Example 28 | 97 | 2.0 | 2.0 | toluene | 9.6 | 30 | 3 | 0 | 96 | 3 | 1 | 95.8 |
| Reference Example 29 | 97 | 2.0 | 2.0 | toluene | 2.0 | 30 | 3 | 0 | 97 | 2 | 0 | 97.5 |
| Reference Example 30 | 97 | 2.0 | 2.0 | toluene | 4.0 | 30 | 3 | 0 | 97 | 2 | 1 | 97.7 |
| Reference Example 31 | 97 | 2.0 | 2.0 | toluene | 6.0 | 30 | 3 | 0 | 97 | 3 | 0 | 97.7 |
| Reference Example 32 | 97 | 2.0 | 2.0 | toluene | 8.0 | 30 | 3 | 0 | 96 | 3 | 0 | 97.2 |
| Reference Example 33 | 97 | 2.0 | 2.0 | toluene | 9.6 | 30 | 3 | 0 | 96 | 3 | 0 | 98.0 |

DMA-tol in Table 6 means a compound represented by the following chemical formula.

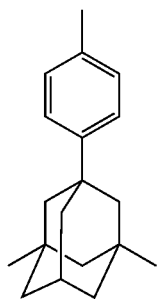

reaction product of DMAO and toluene (DMA-tol)

INDUSTRIAL APPLICABILITY

The present invention is effective in the fields of medicinal products or the like.

The invention claimed is:

1. A method for manufacturing 3,5-dimethyl-1-adamantanamine, comprising:
    (i) reacting 3,5-dimethyl-1-adamantanol with an acid and nitrile in an organic solvent to obtain a reaction solution;
    (ii) adding water to the reaction solution obtained in (i) to obtain 1-amido-3,5-dimethyladamantane; and
    (iii) hydrolyzing 1-amido-3,5-dimethyladamantane obtained in (ii) in the presence of an inorganic base, and an alcohol-containing solvent comprising at least one alcohol selected from the group consisting of 1-butanol, 1-pentanol, 1-hexanol, 1-heptanol, and 1-octanol.

2. The method according to claim 1, wherein the organic solvent in (i) is hydrophobic.

3. The method according to claim 1, wherein the organic solvent in (i) comprises at least one organic solvent selected from the group consisting of an aliphatic hydrocarbon and an aromatic hydrocarbon.

4. The method according to claim 1, wherein a molar ratio of the acid to 3,5-dimethyl-1-adamantanol in (i) is 1 to 10.

5. The method according to claim 1, wherein a molar ratio of the nitrile to 3,5-dimethyl-1-adamantanol in (i) is 1 to 10.

6. The method according to claim 1, wherein the acid used in (i) contains at least one acid selected from the group consisting of sulfuric acid, nitric acid, phosphoric acid, trifluoroacetic acid, and toluenesulfonic acid.

7. The method according to claim 1, wherein the acid used in (i) contains concentrated sulfuric acid.

8. The method according to claim 1, wherein the nitrile used in (i) contains at least one nitrile selected from the group consisting of methane nitrile, acetonitrile, and propionitrile.

9. The method according to claim 1, wherein the inorganic base used in (iii) contains sodium hydrate or potassium hydrate.

\* \* \* \* \*